US007381960B1

(12) United States Patent
Chuang (10) Patent No.: US 7,381,960 B1
(45) Date of Patent: Jun. 3, 2008

(54) IMAGING SYSTEM AND METHOD FOR THE NON-PURE POSITRON EMISSION TOMOGRAPHY

(75) Inventor: Keh-Shih Chuang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 11/558,900

(22) Filed: Nov. 11, 2006

(51) Int. Cl.
*G01T 1/00* (2006.01)
(52) U.S. Cl. .............................. 250/363.03; 250/363.04
(58) Field of Classification Search .......... 250/363.03, 250/363; 600/425, 436
See application file for complete search history.

(56) References Cited

U.S. PATENT DOCUMENTS

| | | | |
|---|---|---|---|
| 6,175,116 B1* | 1/2001 | Gagnon et al. ........ | 250/363.03 |
| 6,303,935 B1* | 10/2001 | Engdahl et al. ........ | 250/363.03 |
| 6,484,051 B1* | 11/2002 | Daniel ..................... | 600/436 |
| 6,963,065 B2* | 11/2005 | Conti et al. ............... | 250/252.1 |
| 2003/0111608 A1* | 6/2003 | Dulmen et al. .......... | 250/363.1 |
| 2004/0069951 A1* | 4/2004 | Jones et al. .............. | 250/369 |
| 2006/0065840 A1* | 3/2006 | Joung et al. ............. | 250/363.05 |

OTHER PUBLICATIONS

Liang Z. and Jaszczak R., Comparisons of Multiple Photon Coincidence Imaging Techniques, Jan. 1990, IEEE Transactions on Nuclear Science, vol. 37, No. 3, pp. 1282-1292.*
High-resolution molecular imaging techniques for cardiovascular research, Benjamin M. W. Tsui, PhD, and Yuchuan Wang, PhD, doi:10.1016/j. nucleard.2005.03.005, p. 261-267.
PET imaging with yittrium-86:comparsion of phantom measurements acquired with different PET scanners before and after applying background subtraction, H. G. Buchholz, Herzog, G. J. Forster, H. Reber, O. Nickel, F. Rosch, P. Bartenstein, /Accepted: Dec. 7, 2002/Published online: Feb. 26, 2003 European Journal of Nuclear Medicine and Molecular Imaging vol. 30, No. 5, May 2003, p. 716-720.
An Integrated PET-Spect Small Animal Imager: preliminary results, A Del Guerra, Senior Member, IEEE, C. Damiani, G. Di Domenico, A. Motta, M. Giganti, R. Marchesint, A. Piffanelli, N. Sabba, L. Sartori and G. Zavattini, IEEE Transations on Nuclear Science, vol. 47, No. 4, Aug. 2000, p. 1537-1540.
Quantitative dynamic Cardiac $^{82}$Rb PET Using Generalized Factor and Compartment Analyses, Georges El Fakhri, PhD; Arkadiusz Sitek, PhD, Bastien Guerin, MSc; Marie Foley Kijweski, ScD; Marcelo F. Di Carli, MD; and Stephen C. Moore, PhD, The Journal of Nuclear Medicine, vol. 46, No. 8, Aug. 2005, p. 1264-1671.

(Continued)

*Primary Examiner*—David P. Porta
*Assistant Examiner*—David S Baker (57) ABSTRACT

Disclosed is an imaging system and method for the non-pure positron emission tomography (NPET). The NPET comprises a PET subsystem to detect the annihilated photons, and a SPECT subsystem to detect the associated gamma. These two subsystems are connected by a triple coincidence circuit. The source position can be determined through detection of the three photons using the triple coincidence circuit. As long as these three photons are simultaneously detected and their energies are right, the source position is directly calculated and located on the intersection of an associated line and an annihilated line. The present invention provides good temporal resolution and quantitative analysis. It immunes to scatter and random events and achieves a high signal-to-noise ratio. Real imaging is also possible in the NPET system.

3 Claims, 11 Drawing Sheets

OTHER PUBLICATIONS

Three-Gamma Annihilation Imaging in Positron Emission Tomography, Krzysztof Kacperski, Nicholas M. Spyrou, and F. Alan Smith, IEEE Transactions on Medical Imaging, vol. 23, No. 4, Apr. 2004, p. 525-529.

Performance of a block detector PET scanner in imaging non-pure positron emitters-modelling and experimental validation with $^{124}$I, S Robinson, P J Julyan, D L Hastings and J Zweit, in final form Oct. 22, 2004, Published Dec. 6, 2004, Online at stacks.iop.org/PMB/49/5505, p. 5505-5528.

Addressing the Third Gamma Problem in PET, M. J. Schueller, T. L. Mulnix, B. T. Christian, M. Jensen, S. Holm, T. R. Oakes, A. D. Roberts, D. W. Dick, C. C. Martin, and R. J. Nickles, IEEE Transactions on Nuclear Science, vol. 50, No. 1, Feb. 2003, p. 50-52.

PET quantitation and imaging of the non-pure positron-emitting iodine isotope $^{124}$I, H. Herzog, L. Tellmann, S. M. Qaim, S. Spellerberg, A. Schmid, H. H. Coenen, received in revised form Dec. 7, 2001; accepted Dec. 13, 2001, p. 673-679.

Improved Quantification for Tc-94m PET Imaging, W. Craig Barker, Lawrence P. Szajek, Shielah L. Green, and Richard E. Carson, IEEE Transactions on Nuclear Science, vol. 48, No. 3, Jun. 2001, p. 739-742.

Quantitative Imaging of bromine-76 and yttrium-86 with PET: A method for the removal of spurious activity introduced by cascade gamma rays, Bradley J. Beattie, Ronald D. Finn, Keith S. Pentlow, Medical Physics, vol. 30, No. 9, Sep. 2003, p. 2410-2423.

* cited by examiner

IMAGING SYSTEM AND METHOD FOR THE NON-PURE POSITRON EMISSION TOMOGRAPHY

FIELD OF THE INVENTION

The present invention generally relates to an imaging system and method for the non-pure positron emission tomography (NPET), which may be used to determine the source position through the detection of three photons.

BACKGROUND OF THE INVENTION

Because of its high sensitivity and specificity for detecting a wide range of cancers in oncology, the positron emission tomography (PET) system is becoming very popular for diagnostic study. Coincident detection in the PET system provides the projection sampling which can be reconstructed to yield tomographic images. The primary advantage of PET is its ability to quantify the metabolism activity inside the body.

Figure 1:
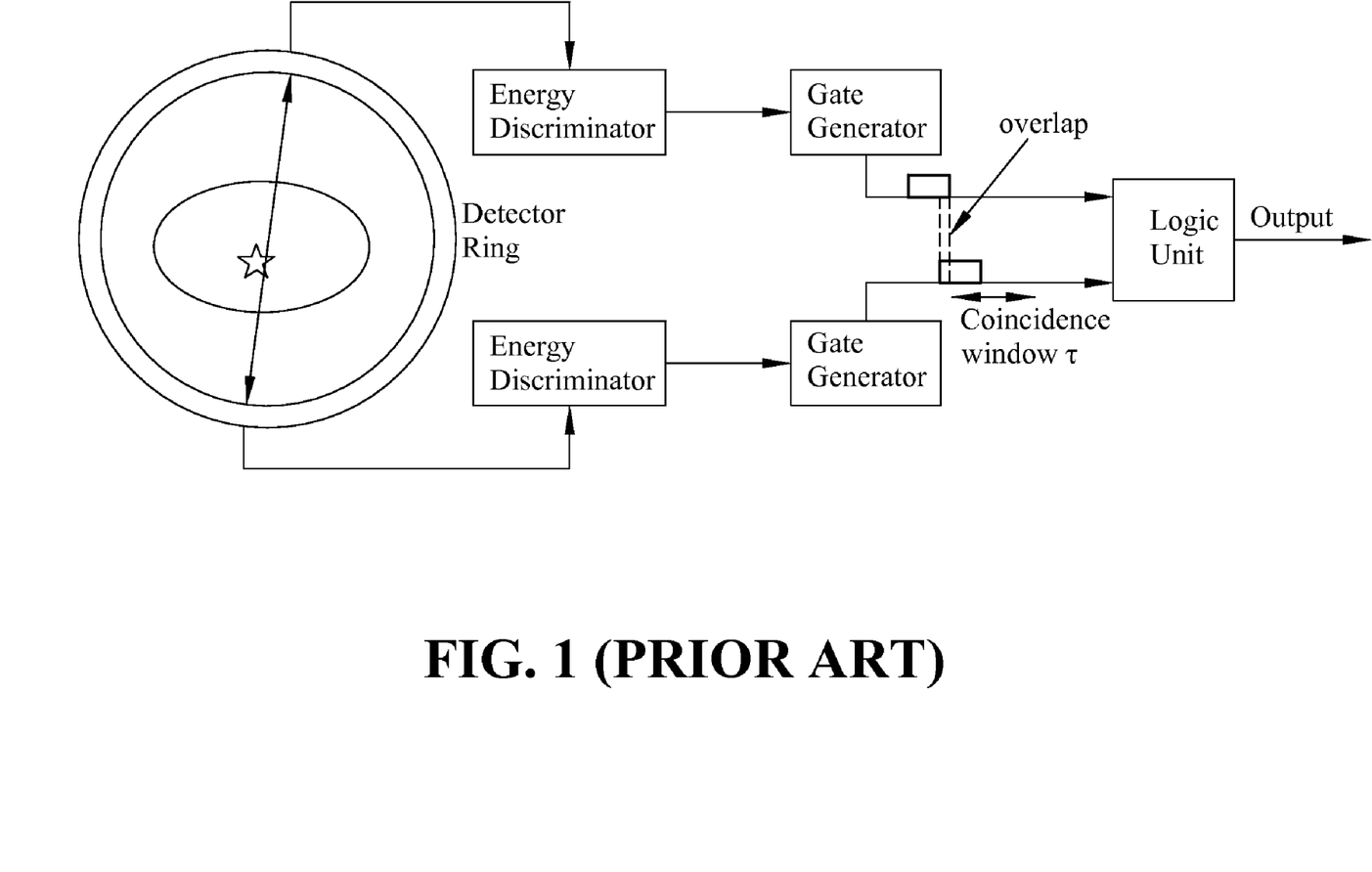
FIG. 1 shows a conventional PET system with the coincidence circuitry.

FIG. 1 shows a conventional PET system with the coincidence circuitry. The PET system utilizes coincident detection of a pair of photons generated by the annihilation of the positron and electron. It includes hundreds of detectors arranged in a ring shape and positioned around an object being tested. Every two detectors are connected by the coincidence circuitry. When two photons are detected at the same time (<12 ns), it is called a coincidence event. The incident direction of photons is the line that connects these two detectors. Many coincidence events can be obtained after scanning for a long time. The whole distribution of emitting sources can be computed and obtained by image reconstruction methods, such as filter backprojection (FBP) and maximum likelihood expectation maximization (MLEM).

Currently, the spatial resolution of a PET system is limited by the high 511-keV photon energy, non-colinearity of the annihilation photons, positron range, and detector technology. A typical small animal PET system provides an absolute sensitivity of approximately 4% and an intrinsic resolution of approximately 1.6 to 1.8 mm (Tsui and Wang 2005).

High-resolution small animal single photon emission computed tomography (SPECT) imaging is possible through the use of pinhole collimation at a much lower cost than small animal PET. There is no theoretic limit of the achievable spatial resolution, it is possible to achieve approximately 1 mm of spatial resolution. The pinhole SPECT requires a heavy collimated detector to rotate around the object and a small misalignment in the setup can generate artifact. Note that to improve the sensitivity, multiple pinholes collimator can be employed. Artefacts can be arisen from overlapping projections in multi-pinhole reconstruction for such a conventional SPECT.

So far $^{18}$FDG (fluoro-deoxyglucose) is the most commonly used pharmaceutical for PET study. However, the absorption of FDG is mainly due to the absorption of glucose for the metabolic process and is not organ specific. Furthermore, the short half-life of $^{18}$F limits its usage when a long observation is needed.

In recent years, there is a growing interest in the use of non-pure positron emitters. The use of non-pure positron emitters as an alternate to $^{18}$F for PET study is gaining popularity in diagnostic or therapeutic radiopharmaceuticals due to their longer half-lives and target specific properties (Herzog et al 2002). The long half-life is advantageous for developing radiochemical syntheses and allows the tracing of slow biochemical processes.

Of particular interest are $^{38}$K, $^{52m}$Mn, $^{60}$Cu, $^{94}$mTc, and $^{124}$I. These isotopes are not pure positron emitters; high energy gamma rays (called associated gamma rays) are emitted simultaneously with the positron that can be scattered down to the primary energy window and give rise to random coincidence events. These detected photons are not angularly correlated and therefore contain no information regarding the location of their events. This downgrades the PET performance. The isotropic property of the associated gamma rays causes the events to be evenly distributed across the entire sinogram and contributes only a low frequency background to the reconstructed image.

Robinson et al (2004) claimed that non-pure emitters are not suitable for 3D mode due to the potentially large increase in the observed scatter fraction expected, in "Performance of a block detector PET scanner in imaging non-pure positron emitters—modelling and experimental validation with $^{124}$I", *Phys. Med. Biol.* 49 5505-28. Schueller et al (2003) investigated the problem of third gamma in PET and concluded that no benefit comes from the third gamma, in "Addressing the third gamma problem in PET", *IEEE Trans. Nucl. Sci.* 50 50-2.

Figure 2:
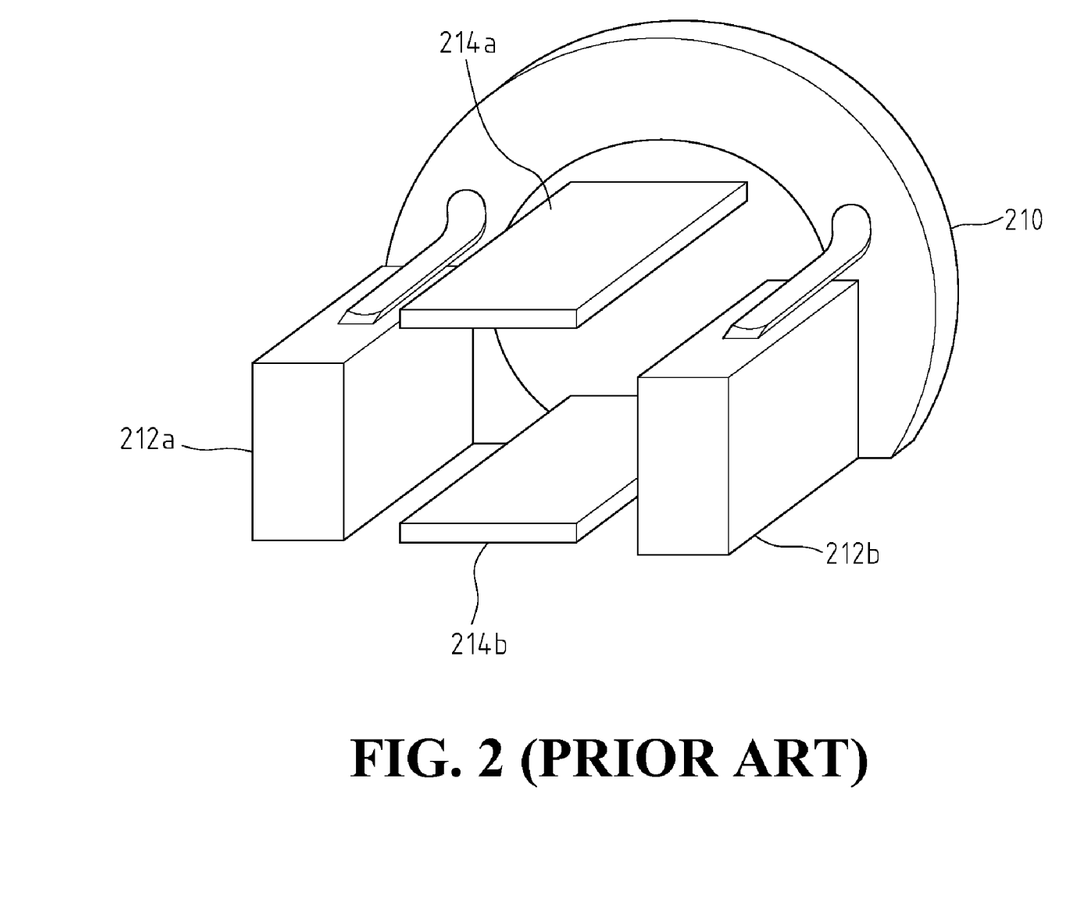
FIG. 2 shows a conventional combination PET/SPECT nuclear imaging system.

Guerra et al (2000) invented a PET-SPECT system. The PET-SPECT system is not stationary, but requires 180° rotations of gantry to collect all the data. In the disclosure of U.S. Pat. No. 6,303,935, John C. Engdahl et al invented a combination PET/single photon (SPECT or planar) nuclear imaging system. As shown in FIG. 2, the system utilizes a pair of dedicated PET detectors 212a-212b and at least one dedicated single photon detectors 214a-214b mounted on a single gantry 210. The PET detectors 212a-212b perform only high energy PET imaging, while single photon detectors 214a-214b perform only low single photon imaging. Simultaneous PET/single photon imaging studies can be carried by the single system. The photon detectors also may be removable and mountable on a separate, dedicated single photon imaging gantry.

Kacperski et al (2004) also proposed a PET system utilizing the coincident detection of 3γ decays from positron annihilation. By the law of energy and momentum conservation, the source position can be determined. However, the accuracy of source positioning is greatly dependent upon the energy resolution of the detectors and the 3γ decay is a rare event which is about 2 orders less than regular 2γ decays.

There are some examples of the important non-pure positron emitters. $^{76}$Br (bromine-76) is used for the investigation in molecular imaging (Beattie et al 2003). $^{86}$Y (yttrium-86) is used for dose estimation in patient therapies with $^{90}$Y-labeled radiopharmaceuticals (Buchholz et al 2003). $^{82}$Rb allows the assessment of absolute myocardial perfusion as well as coronary flow reserve (Fakhri et al 2005). The positron emitter $^{94m}$Tc can be used to improve quantification of tracers currently labeled with $^{99m}$Tc (Barker et al 2001). $^{124}$I PET is utilized in comparative studies in which diagnostic or therapeutic radiopharmaceuticals labeled with the $^{123}$I or $^{131}$I (Herzog et al 2002). The long half-life of these non-pure positron emitters is advantageous for developing radiochemical syntheses that allows the tracing of slow biochemical processes which cannot be adequately examined by the commonly used short-lived positron emitters.

SUMMARY OF THE INVENTION

The present invention provides a novel imaging system called non-pure positron emission tomography that utilizes the associated gamma ray to aid source localization. The NPET system is based on the fact that the source position can be determined through detection of the three photons (2 annihilation photons and 1 associated gamma) using a triple coincidence circuit.

The NPET system of the present invention consists of two types of detection systems, referred to a PET subsystem and a SPECT subsystem. These two subsystems are connected by a triple coincidence circuit. The PET subsystem detects the annihilated photons. The SPECT subsystem includes at least one collimator to detect the associated gamma with the direction specified by the collimator.

The three photons (two annihilation photons and an associated gamma) are emitted simultaneously from the source and they are on two straight lines, and these two lines are intersected at the site where they are originated from. As long as these three photons are detected in the same time and their energies are right, the source position is located on the intersection of the incoming direction of the associated gamma and the line of annihilated photons. The localization mechanism of geometric intersection enables the rejection of scattered and random coincidence events and also helps to improve the collimator resolution.

An advantage of the present invention is that source position is calculated directly from the detected three photons, without 180° data acquisition or image reconstruction. This makes real time imaging possible. The present invention also provides good temporal resolution and quantitative analysis. It immunes to scatter and random events and achieves a high signal-to-noise ratio (SNR).

The foregoing and other features, aspects and advantages of the present invention will become better understood from a careful reading of a detailed description provided herein below with appropriate reference to the accompanying drawings.

DETAILED DESCRIPTION OF THE PREFERRED EMBODIMENTS

Figure 3:
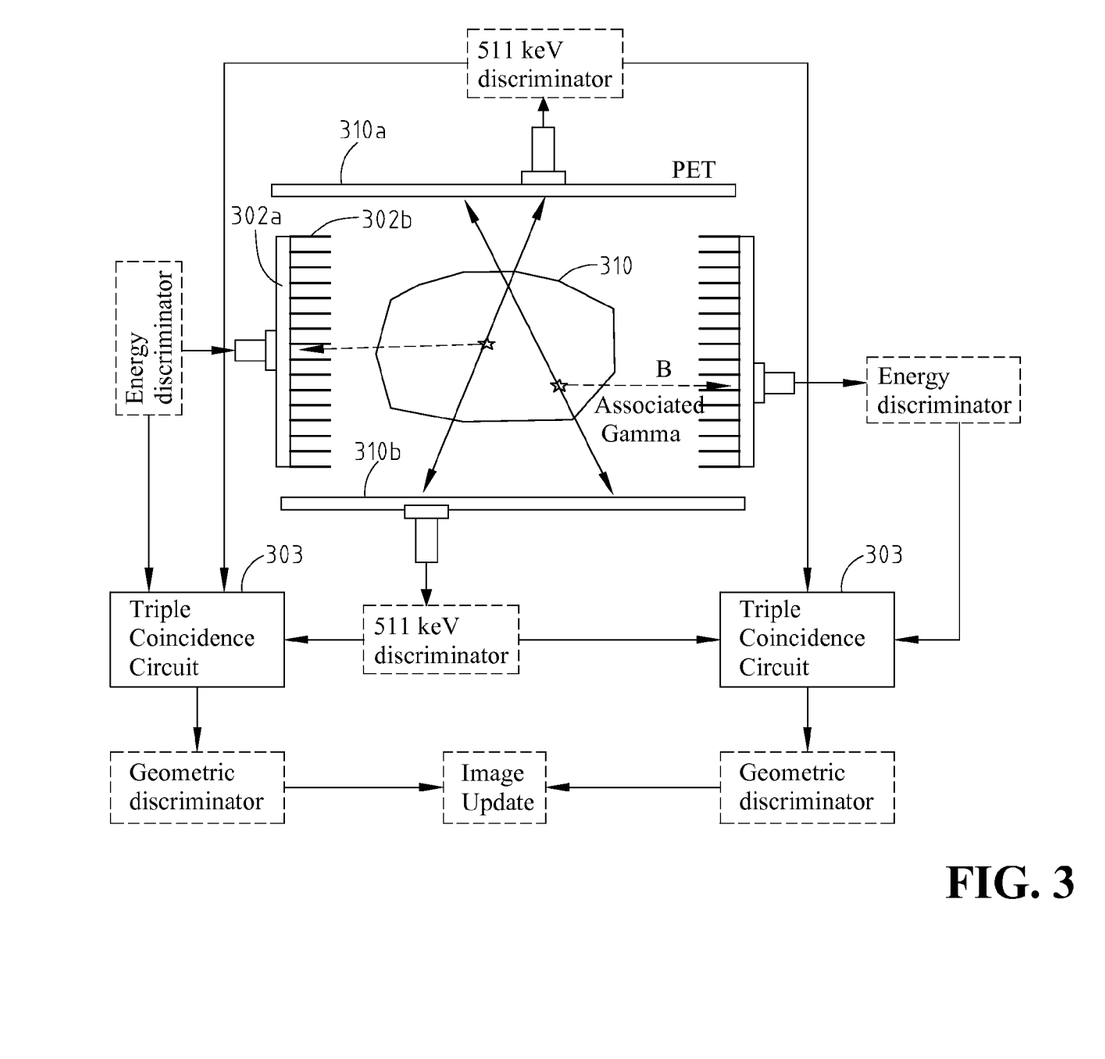
FIG. 3 shows an embodiment according to the present invention.

FIG. 3 shows an embodiment according to the present invention. Referring to FIG. 3, the NPET system consists of two types of detection systems. The first type of detection system is referred to a PET subsystem and the second type of detection system is referred to a SPECT subsystem. These two subsystems are connected by a triple coincidence circuit 303. The PET subsystem simultaneously detects two annihilated photons (511 KeV). The direction of the annihilated photons (called annihilation line) is along the line of response (LOR) connected by the two detectors that coincidentally intercept the photons. The SPECT subsystem is a detector 302a with at least one collimator 302b to detect an associated photon with the direction specified by the collimator 302b. During scanning an object 310, the NPET system is placed to surround the object 310. The position of a point source is determined through the detection of the three photons. The signals from these three photons after an energy discriminator are fed into the triple coincidence circuit 303.

Without loss of the generality, the PET subsystem may be a pair of parallel detectors as 310a-310b shown in FIG. 3, or a detector ring (described later), The collimator 302b may be one or more parallel collimators, one or more collimators with multiple pinholes, . . . , etc. The collimator 302b shown in FIG. 3 is a parallel collimator. In the case, the direction of the detected associated gamma ray (called associated line) is determined by the collimator. These two subsystems, PET subsystem and SPECT subsystem, may be perpendicular to each other, as shown in FIG. 3.

As long as these three photons are detected in the same time and their energies are right, the source position is located on the intersection of the incoming directions of the associated line and the annihilated line. The localization mechanism of geometric intersection enables the rejection of scattered and random coincidence events and also helps to improve the collimator resolution. The energies of these three photons are quite high. High Z materials, like BGO or LSO may be employed as detectors to increase the detection efficiency.

Figure 4A:
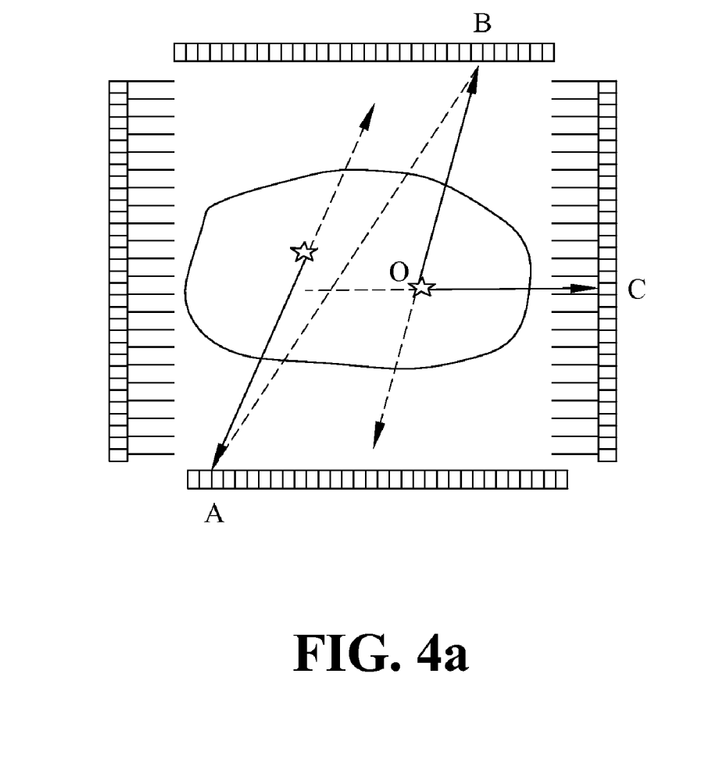
FIG. 4a illustrates a random coincidence event for the imaging.
Figure 4B:
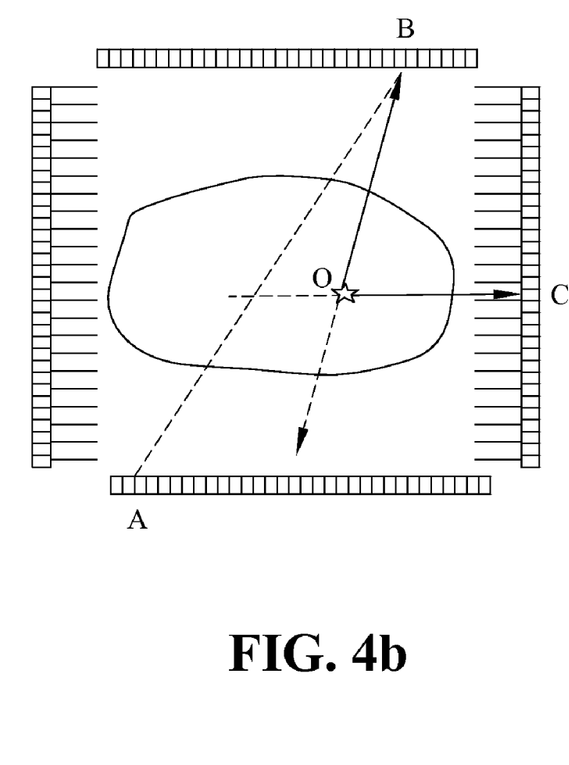
FIG. 4b illustrates a scattered coincidence event for the imaging.
Figure 6:
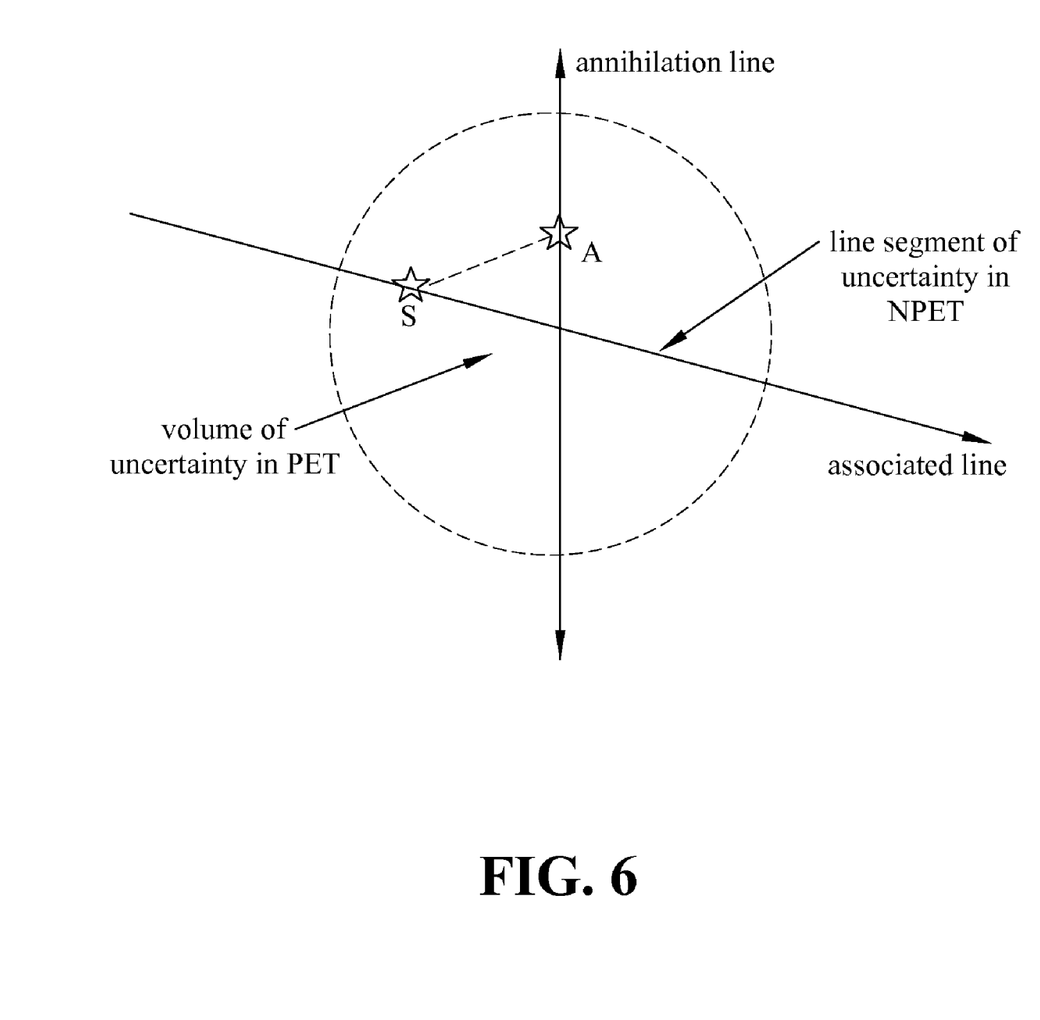
FIG. 6 shows the comparison of the uncertainty in conventional PET system and the NPET system of the present invention due to the positron range.
Figure 7:
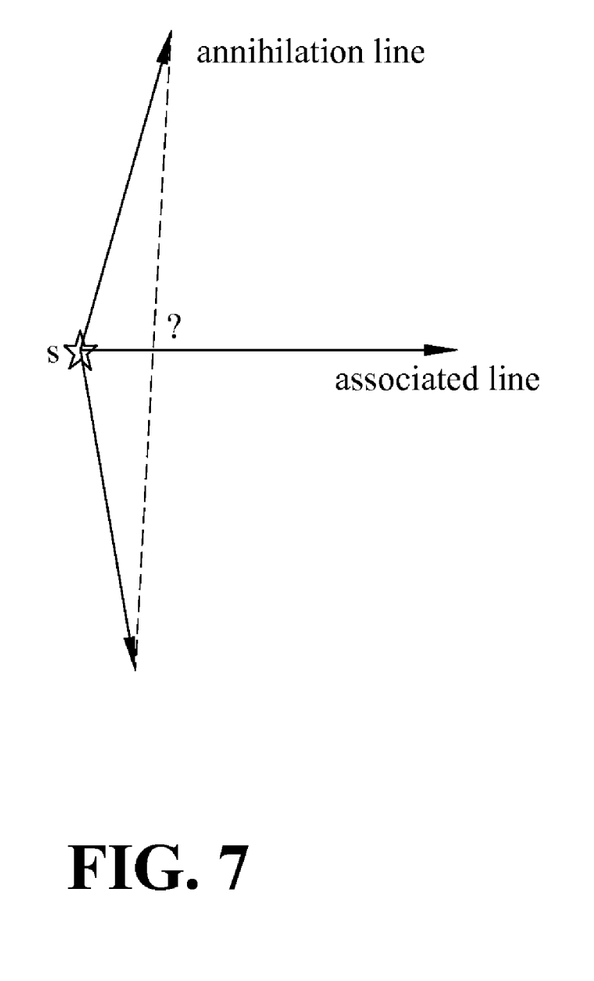
FIG. 7 illustrates that the non-colinearity shifts the annihilation line away from the photons emission site when annihilation occurs.

The random and scattered coincidence events, as respectively shown in FIGS. 4a-4b, often occur in a conventional PET system. The characteristic of these two events is that their line of response (LOR) does not pass through their origins. As a result, this LOR (AB) does not have intersection with the associated line OC in a 3-D geometry as the associated gamma is originated from the source. Same argument is true when the associated gamma is scattered before its detection. The NPET system of the present invention has an inherent non-true (scattered plus random coincidence) event free mechanism. This geometric discriminator can be used to reduce the effects caused by the positron range and non-colinearity of the annihilation photons. FIG. 6 shows the comparison of the uncertainty in conventional PET system and the NPET system of the present invention due to the positron range. FIG. 7 illustrates that the non-colinearity shifts the annihilation line away from the photons emission site when annihilation occurs.

The NPET system of present invention uses a geometric discriminator for the rejection of the non-true events. Since direct position in 3-D is possible, it enables the reconstruction process to be bypassed and removes the process that amplifies the noise in the image. With the automatic reduction in the noise, the advantage of high SNR in the NPET system is obvious.

Due to the geometric localization mechanism, the spatial resolution is not uniform; the vertical spatial resolution is limited by the SPECT subsystem while the horizontal resolution is imposed by the PET subsystem. The spatial resolution can be made more uniform and smaller by employing additional scans at different angles, such as a 90° rotation. The geometric mean of the two images, $I_0(x,y)$ and $I_{90}(x,y)$, by dual scans (0° and 90°) is the new image $$I(x,y)=\sqrt{I_0(x,y) \times I_{90}(x,y)}.$$

Figure 5:
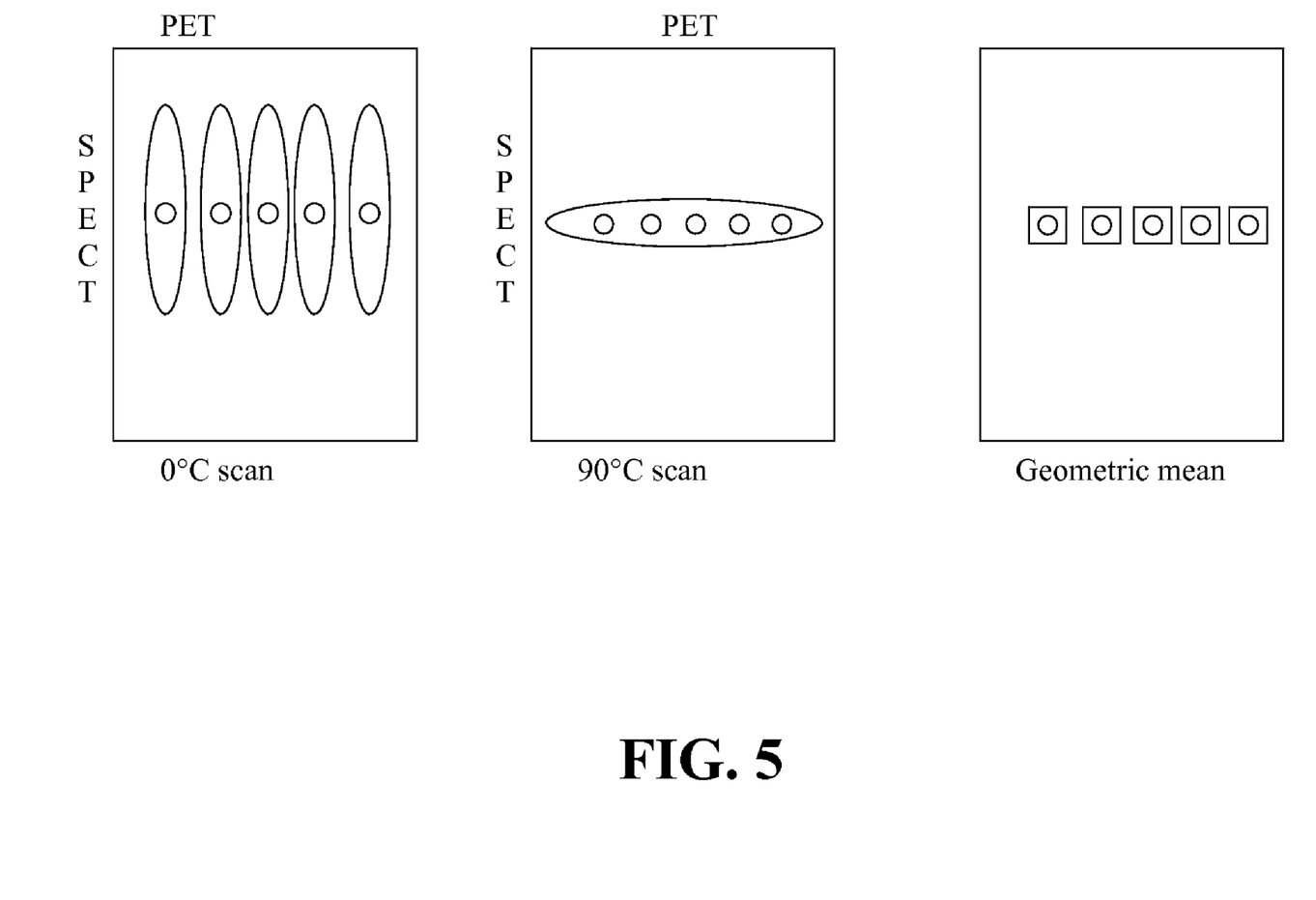
FIG. 5 illustrates the geometric mean of dual scans to make a uniform and smaller spatial resolution according to the present invention.

This is illustrated in FIG. 5.

In the present invention, two lines are said to intersect if their minimum distance is less than a threshold. In this invention, the threshold is used to control the spatial resolution of the system and set to be the size of the collimator holes. The NPET system of the present invention obtains (neglecting the finite measurement accuracy) full information about the source position from a single event, rather than a LOR in a conventional PET system. This can be regarded as perfect electronic registration. The registration solves the intersection of two lines and can be performed for each event independently. The image can be updated on-line as new events appear. However, a conventional PET system needs to wait for the full image data to be registered and then reconstructed by rather complex reconstruction methods. This real time imaging of the present invention is therefore a significant advantage for certain study, such as diagnosis on brain function.

The quantitative analysis is possible in the NPET system of the present invention. To obtain a quantitative image factor like attenuation or geometric efficiency, addressing normalization is needed. The correction factor is position dependent in the NPET system because of the attenuation of the associated gamma ray. The correction may be achieved by first using a transmission scan, e.g. by a computed tomography (CT), to construct a map of attenuation coefficient. Once an event is detected and its source position is determined, the attenuation of the three photons is calculated from the attenuation map and corrected for the activity concentration.

Conventional PET systems use energy discriminators to reject the scattered radiation. As a result, high energy resolution of the crystal is critical. In the NPET system of the present invention, rejecting scattered events is achieved through the geometric discriminator, and the energy resolution is not so critical.

Figure 8:
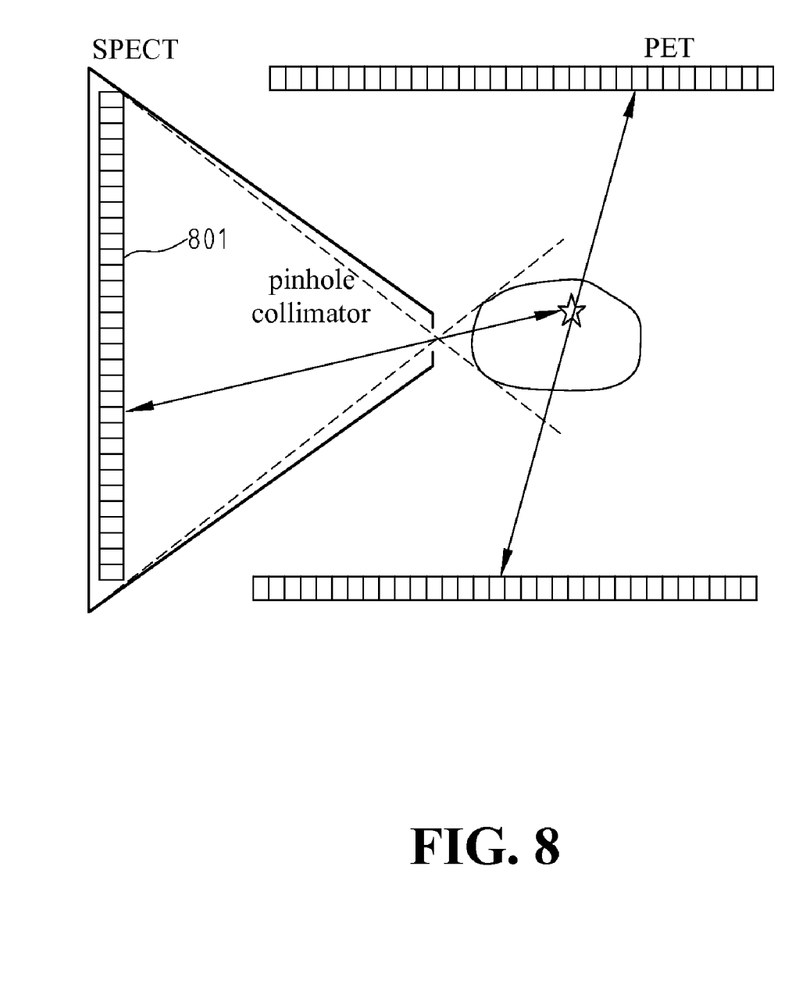
FIG. 8 shows an example that a multiple pinholes collimator is employed in the NPET system according to the present invention.

In the embodiment of FIG. 3, the pinhole collimator may be used in the SPECT subsystem to enhance spatial resolution. To increase sensitivity, a multiple pinholes collimator may be employed. FIG. 8 shows an example that a multiple pinholes collimator 801 is employed in the NPET system according to the present invention. Even though there are multiple possible source locations for each detected photon, through the use of geometric discrimination mechanism it is easy to locate the actual position and the overlapping caused by the multiple pinholes can be solved easily.

Figure 9:
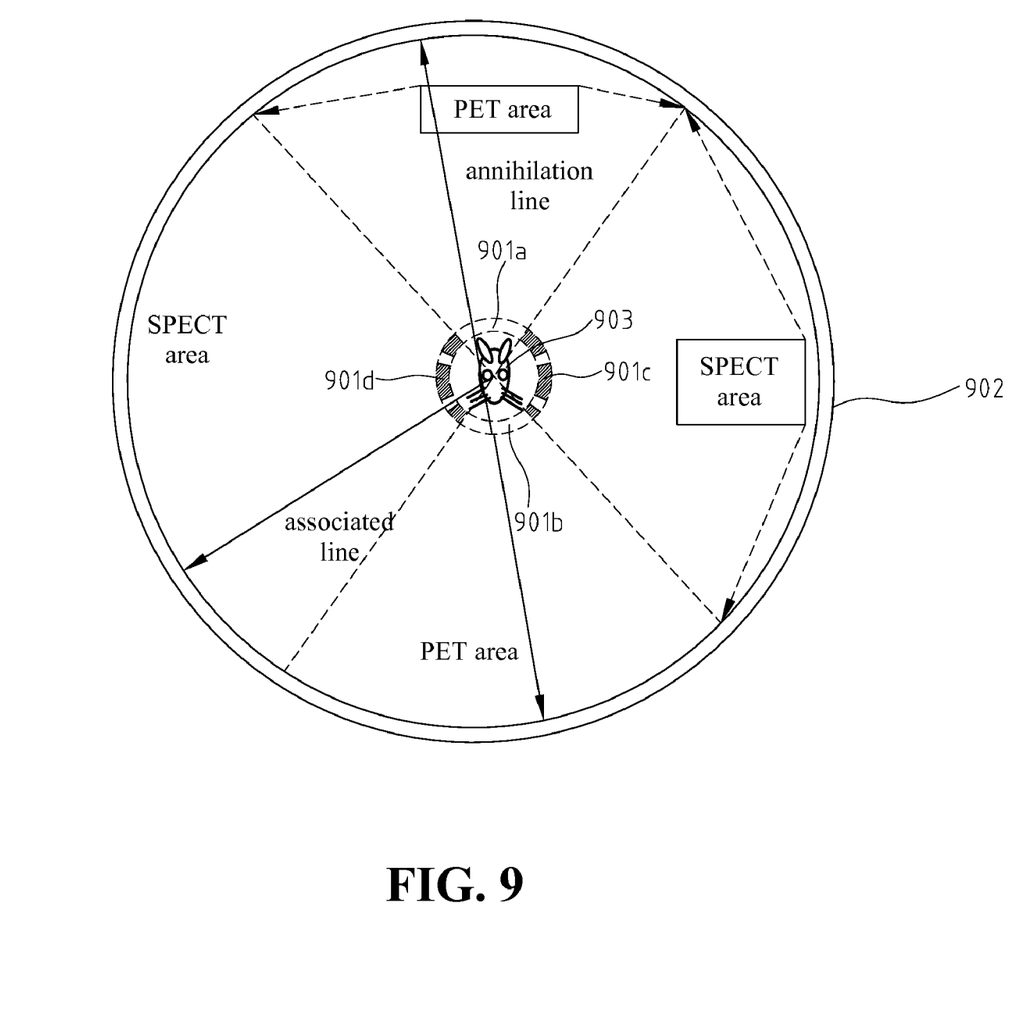
FIG. 9 shows an example for an animal NPET system according to the present invention.

According to the present invention, an animal NPET system may be achieved by using a conventional PET system, such as a detector ring 902 with a cylindrical pinhole collimator formed by four quarters 901a-901d, as shown in FIG. 9. Two quarters 901a and 901b (upper and lower parts for the PET area) of the collimator are empty to allow annihilation photon to go through freely. The other two quarters 901c and 901d (left and right parts for the SPECT area) of the collimator are multiple pinholes to collimate the associated photon to go through desired direction. Of course, a triple coincidence circuit (not shown) is also necessary. To obtain a uniform resolution in all directions, the cylindrical pinhole collimator may simultaneously scan and rotate. During scanning an object 903, the cylindrical pinhole collimator is placed between the object 903 and the detector ring 902.

Figure 10A:
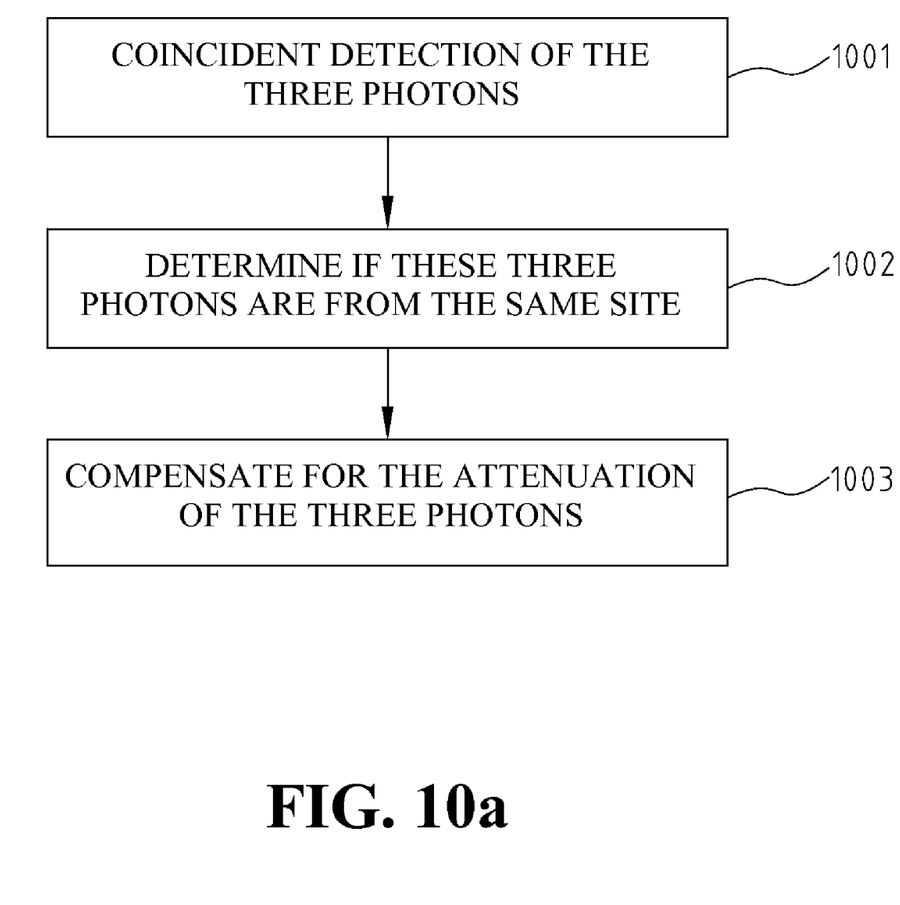
FIG. 10a and FIG. 10b show a flow of the imaging method implemented in the NPET system shown in FIG. 3.
Figure 10B:
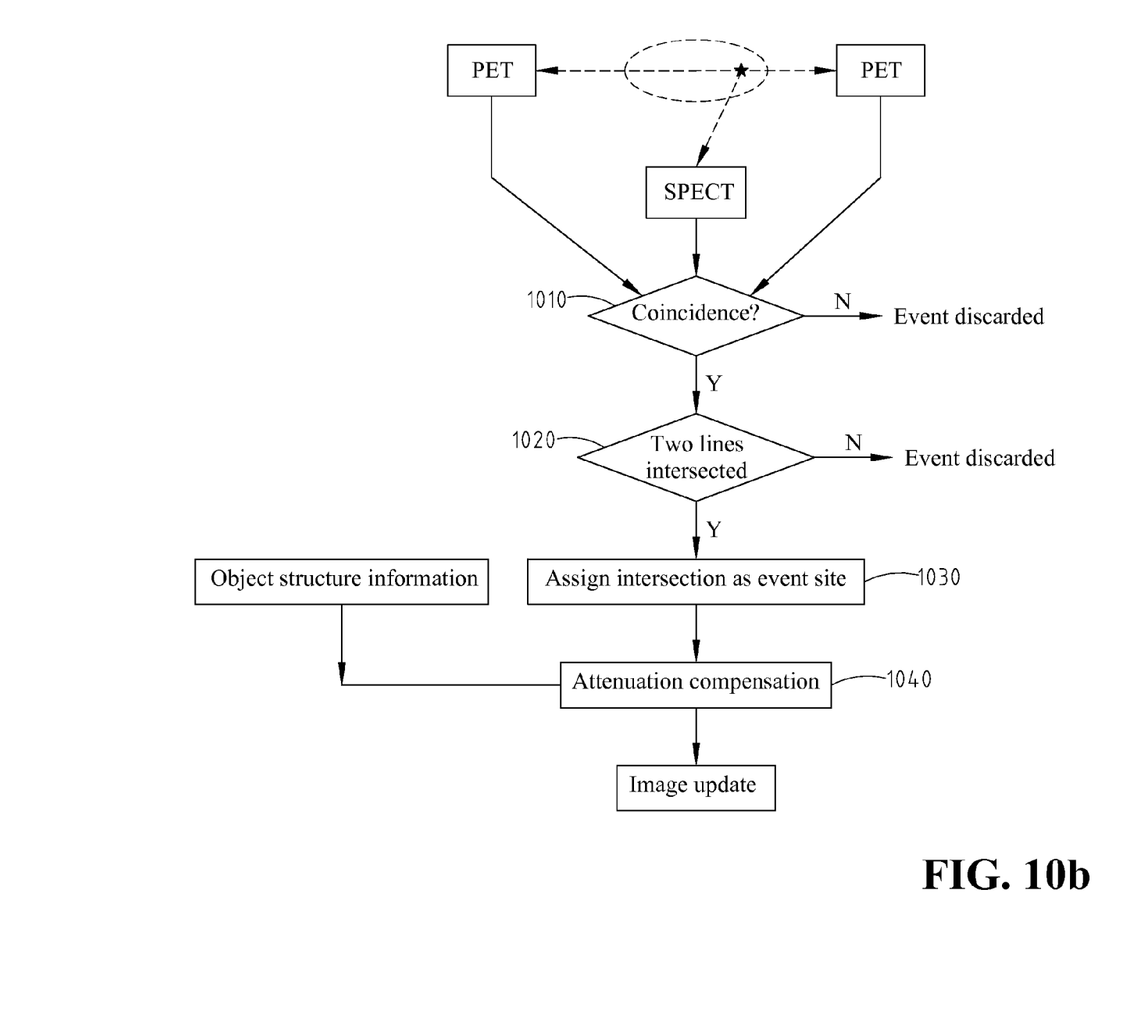

The imaging method implemented in the NPET system shown in FIG. 3 may comprise the following three major steps, as shown in FIG. 10a. The first step 1001 is the coincident detection of the three photons. The second step 1002 is to determine if these three photons are from the same site. The third step 1003 is to compensate for the attenuation of the three photons using an attenuation map obtained from a transmission scan. FIG. 10b shows a flow chart illustrating more detailed operations for the imaging method in FIG. 10a.

Referring to FIG. 10b, the three photons simultaneously are detected by the PET subsystem and the SPECT subsystem, and the coincidence of the three photons is checked, as shown in step 1010. If the three photons are not coincided, the event is discarded. If the three photons are coincided, whether the annihilation line and the associated line are intersected is further detected, as shown in step 1020. It is also discarded for the event that the two lines are not intersected. If the two lines are intersected, the location of the event site is assigned as the intersection, as shown in step 1030.

As mentioned earlier, the quantitative analysis is possible in the NPET system of the present invention. To achieve the attenuation compensation shown in step 1040, the object structure information is provided and an attenuation map is constructed from a transmission scan. Accordingly, the image can be updated on-line.

In the conventional PET system proposed by Kacperski et al (2004), it utilizes the coincident detection of 3γ decays from positron annihilation. By the law of energy and momentum conservation, the source position can be determined. However, the accuracy of source positioning is greatly dependent upon the energy resolution of the detectors and the 3γ decay is a rare event which is about 2 orders less than regular 2γ decays. In contrast, the energy resolution in the NPET system of the present invention is not so critical and the occurrence probability of the associated gamma is almost the same as positron emission.

From the outlook of the structure, the NPET system of the present invention is similar to the PET-SPECT system proposed by Guerra et al (2000). The main differences are: (1) the NPET system of the invention uses a triple coincidence circuit to detect the three photons simultaneously; and (2) the NPET system of the invention is stationary while the PET-SPECT needs 180 rotations to collect all the data.

There are two drawbacks of the pinhole SPECT, namely the poor sensitivity and rotation orbit misalignment. The pinhole SPECT requires a heavy collimated detector to rotate around the object and a small misalignment in the setup can generate a displaced center of rotation and produce artifacts. Although the NPET system of the present invention incorporates a pinhole collimator, it does not have these disadvantages because it uses multiple pinholes to increase the sensitivity and it does not require any rotation.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. An imaging system for non-pure positron emission tomography (NPET), comprising:
   a detector ring divided into four areas, two of said four areas being positron emission tomography (PET) areas facing each other and the other two areas being single photon emission computed tomography (SPECT) areas;
   a cylindrical pinhole collimator located near the center of said detector ring, said cylindrical pinhole collimator having four sections with two of said four sections being PET sections corresponding to and facing said PET areas, and the other two sections being SPECT sections corresponding to and facing said SPECT areas; and
   a triple coincidence circuit connected to said detector ring;
   wherein said two PET sections of said cylindrical pinhole collimator are empty to allow annihilated photons emitted from a point source located inside said cylindrical pinhole collimator to go through, said two SPECT sections of said cylindrical pinhole collimator comprise multiple pinholes to collimate associated photons emitted from said point source, and said triple coincidence circuit detects and processes triple coincidence data of two annihilated photons and an associated photon emitted from said point source.

2. The imaging system as claimed in claim 1, wherein said detector ring is made of high Z materials.

3. The imaging system as claimed in claim 1, further comprising an energy discriminator connected between said detector ring and said triple coincidence circuit.

* * * * *